United States Patent

Taguchi et al.

Patent Number: 5,731,268
Date of Patent: Mar. 24, 1998

[54] METHOD FOR IMPROVEMENT AND PREVENTION OF DRY SPOTS

[75] Inventors: Kenichi Taguchi; Takumi Shirataki, both of Kubiki-mura; Kinya Ogawa, Tokyo; Kouji Kinoshita, Takefu, all of Japan

[73] Assignee: Shin-EtsuChemical Co., Ltd., Tokyo, Japan

[21] Appl. No.: 642,896

[22] Filed: May 6, 1996

[30] Foreign Application Priority Data

| May 8, 1995 | [JP] | Japan | 7-134806 |
| Oct. 26, 1995 | [JP] | Japan | 7-302183 |
| Mar. 19, 1996 | [JP] | Japan | 8-090418 |

[51] Int. Cl.$^6$ ............... A01N 31/02
[52] U.S. Cl. ............... 504/351; 47/DIG. 10; 71/903
[58] Field of Search ............... 47/DIG. 10; 71/903; 504/351, 353, 118, 116, 140

[56] References Cited

U.S. PATENT DOCUMENTS

| 4,690,589 | 9/1987 | Owa | 405/263 |
| 4,783,342 | 11/1988 | Polovina | 427/4 |
| 5,258,359 | 11/1993 | Kassebaum et al. | 504/206 |
| 5,472,458 | 12/1995 | Ogawa et al. | 47/1.01 |

*Primary Examiner*—S. Mark Clardy
*Attorney, Agent, or Firm*—Townsend & Banta

[57] ABSTRACT

A method for improvement (treatment) and prevention of dry spots on the grass surface of a golf course comprising sprinkling of an acetylene alcohol derivative (s) or sprinkling of it along with a water soluble polymer water retentive agent on the grass surface. Also, a method for prevention of dry spots on the grass surface of a golf course comprising sprinkling of a water soluble polymer water retentive agent(s) on the grass surface.

6 Claims, No Drawings

METHOD FOR IMPROVEMENT AND PREVENTION OF DRY SPOTS

RELATED APPLICATIONS

This application claims the priority of Japanese Patent applications No.7-134806 filed on May 8, 1995, No. 7-302183 filed on Oct. 26, 1995 and No. 8-90418 filed on Mar. 19, 1996, which are incorporeted herein by reference.

BACKGROUND OF THE INVENTION

1. Field of the Invention

This invention relates to a method of preventing dry spots from developing on the grass surface of a golf course and improving (treating) the already developed dry spots to maintain the golf course in a well managed condition.

2. The Prior Art

Recently, development of dry spots on sand bent grass greens of golf courses has been a serious problem. A "dry spot" is an irregularly shaped area damaged by dryness due to an unknown cause. If the symptoms are advanced, the grass will eventually die.

The cause of dry spots can be consolidation of the soil, uneven water sprinkling, washing off of rain and sprinkled water and water repellency of the soil, of which water repellency of the soil is the most frequent cause. Once the water content of the soil is reduced and water repellency is developed, it becomes hard for sprinkled water to permeate and effective water sprinkling becomes difficult. Speculated causes of the water repellency include production of a water repellent substance by microorganisms, but a complete explanation has yet to be given.

Methods which have been tried to prevent dry spots include keeping the water content of the soil from decreasing, i.e. thorough water sprinkling management, sprinkling of a wetting agent and improvement in the wetting properties of the soil. However, there were following problems: thorough sprinkling management required a significant workforce, securing enough water was difficult in some areas, and, as for sprinkling of a commercial wetting agent, there was a problem in the duration for which the effect lasts and an increase in the number of sprinklings lead to excess foaming, requiring use of a defoaming agent.

BRIEF SUMMARY OF THE INVENTION

Based of the problems mentioned above, the inventors conducted earnest research and discovered that sprinkling an acetylene alcohol derivative on the grass surface could effectively prevent development of dry spots with lesser amounts than the conventional wetting agents and could also improve already developed dry spots, and additionally discovered that use of a water soluble polymer water retentive agent in addition to said acetylene alcohol derivative could prevent and effectively improve dry spots for a long period of time, thus completing the present invention.

The inventors also discovered that sprinkling only the water soluble polymer water retentive agent on the grass surface without jointly using the acetylene alcohol derivative could prevent development of dry spots, although improvement of already developed dry spots was not possible, and thus completed the present invention.

That is, the present invention provides a method for improvement (treatment) and prevention of dry spots on the grass surface of a golf course comprising sprinkling of an acetylene alcohol derivative (s) on the grass surface.

The present invention also provides a method for improvement and prevention of dry spots on the grass surface of a golf course wherein said acetylene alcohol derivative is a compound prepared by adding ethylene oxide to acetylene glycol.

The present invention also provides a method for improvement and prevention of dry spots on the grass surface of a golf course wherein, when sprinkling said acetylene alcohol derivative, a water soluble polymer water retentive agent is jointly sprinkled.

The present invention also provides a method for improvement and prevention of dry spots on the grass surface of a golf course wherein said water soluble polymer water retentive agent is a water retentive agent made of a cation-modified product of a water soluble polymer.

The present invention also provides a method for prevention of dry spots comprising sprinkling of a water soluble polymer water retentive agent(s) on the grass surface of a golf course.

The present invention also provides a method for prevention of dry spots on the grass surface of a golf course wherein said water soluble polymer water retentive agent is a water retentive agent made of a cationic water soluble polymer.

DETAILED DESCRIPTION

The present invention is described in detail below.

The present invention can prevent development of dry spots on the grass surface of a golf course and also improve and reduce already developed dry spots by sprinkling an acetylene alcohol derivative or by sprinkling it along with a water soluble polymer water retentive agent on the grass surface of a golf course.

Sprinkling only the water soluble polymer water retentive agent on the grass surface without jointly using the acetylene alcohol derivative can prevent development of dry spots, although improvement and reduction of already developed dry spots is not possible. When a cationic water retentive agent is used for the water soluble polymer water retentive agent, development of dry spots can be prevented for a long period of time. When the cationic water retentive agent is used by itself or used jointly the acetylene alcohol derivative, development of dry spots can be prevented for a very long period of time even on rainy days when draining of the sprinkling solution is a concern.

For the acetylene alcohol derivative used in the present invention, for example, acetylene glycol to which ethylene oxide is added, as represented by the following formula:

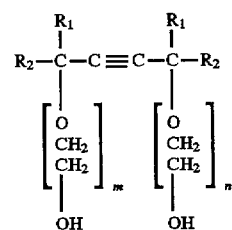

is preferably used. In this formula, $R_1$ denotes a methyl group, $R_2$ denotes a methyl, ethyl, propyl, isobutyl or isoamyl group and such. m and n denote integers where $m+n \geq 1$.

For the water soluble polymer water retentive agent used jointly with the acetylene alcohol derivative or used by itself, for example, cellulose derivatives including methyl cellulose, hydroxylethyl cellulose, hydroxypropylmethyl cellulose, hydroxyethylmethyl cellulose and carboxymethyl cellulose, natural gums including guar gum, xanthan gum and gum arabic, polyvinyl alcohols or their cation-modified products, and prior art water soluble polymers including polyacryl amide, arginic soda, polyethylene glycol and polypropylene glycol can be used without particular limitation. In order to prevent dry spots for a long duration of time, it is preferable to use a cationic water retentive agent which is a cation-modified form of a water soluble polymer.

In the present invention, it is preferable to prepare a 0.01–0.5 wt % aqueous solution of said acetylene alcohol derivative and sprinkle this aqueous solution on the grass surface. The preferable amount should be enough for the treatment solution to permeate into the soil, i.e. 0.01–5.0 liter/m$^2$.

If the concentration of the aqueous solution of the acetylene alcohol derivative is less than 0.01 wt %, then the water may not permeate enough. If it is more than 0.5 wt %, then the effect would not improve and phytotoxity may result.

The water soluble polymer water retentive agent srpinkled jointly or by itself is preferably dissolved in an aqueous solution such that the concentration is 0.001–2.0 wt %. If the concentration is less than this range, then the water retention is not sufficient. It is not preferable to use a concentration above this range because the prevention effect would not change and the viscosity of the aqueous solution would increase.

The reason why the present invention can prevent or improve dry spots is believed to be as follows: when said acetylene alcohol derivative is sprinkled on water repellent soil, it eases the high surface tension of water and accelerates permeation of water into the water repellent soil. When the water soluble polymer water retentive agent is sprayed jointly or by itself, it increases the water retention of the soil permeated with water and thus the water content of the soil increases and this is believed to be the reason why development of dry spots is prevented for a long duration of time. Also, since the polymer infiltrates and is absorbed by the soil, solidification and an increase in water repellency of the soil can be prevented.

The present invention can prevent development of dry spots on the grass surface of a golf course and also improve and reduce already developed dry spots by sprinkling an acetylene alcohol derivative or by sprinkling it along with a water soluble polymer water retentive agent on the grass surface.

Sprinkling only the water soluble polymer water retentive agent on the grass surface without jointly using the acetylene alcohol derivative can prevent development of dry spots, although improvement and reduction of already developed dry spots is not possible.

In particular, then the cationic water retentive agent is used by itself or used jointly the acetylene alcohol derivative, the development of dry spots can be prevented for a very long period of time even on rainy days when draining of the spray solution is a concern.

EXAMPLES

The present invention is described in detail below by referring to examples. The present invention is not limited to the following examples. The concentrations of aqueous solutions are all in the weight percent unit.

[Example 1]

In a golf course in Toyama prefecture, a bent grass nursery was divided into 2 meter square lots in the last ten days of July, and a sprinkling can was used to sprinkle an aqueous solution of the treatment agent on each lot such that the amount would be 2 liter/m$^2$. After this, water was sprinkled every morning for a week and the condition of the grass surface was observed. For the treatment agent, the following (No. 1–4) were used. Changes in the dry spot areas after the sprinkling of each treatment agent are shown in Table 1.

[No. 1: Present invention]

A 0.02% aqueous solution of an acetylene glycol derivative (OLFINE E1004 from Nissin Chemical Industry Co., Ltd.) represented by the following formula:

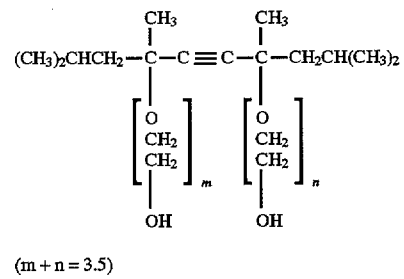

$(m+n=3.5)$

[No. 2: Present invention]

An aqueous solution with 0.02% acetylene glycol derivative (OLFINE E1004 from Nissin Chemical Industry Co., Ltd. ) and 1% cationic hydroxyethyl cellulose (Catinal HC-200 from Toho Chemical Industry Co., Ltd. )

[No. 3: Comparative example]

A 0.1% aqueous solution of a commercial surfactant (a mixture of polyoxyethylene ester of a cyclic acid, polyoxyethylene ether of alkylated phenol and a defoaming agent)

[No. 4: Comparative example]

No treatment agent: water

Changes in the ratio of the dry spot area and the total grass surface are shown in Table 1.

TABLE 1

| | Ratio of the dry spot area and the total grass surface (%) | |
|---|---|---|
| Sample No. | Before the sprinkling of the treatment agent | One week after the sprinkling of the treatment agent |
| 1 | 18 | 0 |
| 2 | 21 | 0 |
| 3 | 18 | 10 |
| 4 | 19 | 40 |

The above results show that the method of the present invention which sprinkles an aqueous solution of an acetylene alcohol derivative has a greater effect of improving dry spots with a lesser amount added than the commercial example in which a commercial surfactant is sprinkled.

[Example 2]

In a bent grass nursery in the same golf course as in Example 1, the amount of water sprinkling was adjusted, starting from the last ten days of July, to create a test area (A) with a high water content and test areas (B and C) with a low water content. These test areas were divided into 2 meter square lots. On each lot, an aqueous solution of one of the treatment agents (No. 1–6) described below was sprayed with an atomizer such that the amount would be 2 liter/m$^2$. After this, a 5 mm per unit area of water sprinkling was done every 7 days and development of dry spots on the grass surface was observed. The number of days passed before dry spots developed after spraying of the aqueous solution of each treatment agent is shown in Table 2.

[No. 1: Present invention]

An aqueous solution with 0.02% acetylene glycol derivative (OLFINE E1004 from Nissin Chemical Industry Co., Ltd.) and 1% cationic hydroxyethyl cellulose (Catinal HC-200 from Toho Chemical Industry Co., Ltd.)

[No. 2: Present invention]

An aqueous solution with 0.02% acetylene glycol derivative (OLFINE E1004 from Nissin Chemical Industry Co., Ltd.) and 1% cationic hydroxyethyl cellulose (Metholose 90 SH-4000 from Shin-Etsu Chemical Co., Ltd.)

[No. 3: Present invention]

A 1% aqueous solution of cationic hydroxyethyl cellulose (Catinal HC-200 from Toho Chemical Industry Co., Ltd.)

[No. 4: Present invention]

A 0.02% aqueous solution of acetylene glycol derivative (OLFINE E1004 from Nissin Chemical Industry Co., Ltd.)

[No. 5: Comparative example]

A 0.1% aqueous solution of a commercial surfactant (a mixture of polyoxyethylene ester of a cyclic acid, polyoxyethylene ether of alkylated phenol and a defoaming agent)

[No. 6: Comparative example]

No treatment agent: water

The number of days passed before dry spots developed after spraying of the aqueous solution of each treatment agent is shown in Table 2.

TABLE 2

| Test area | Number of days before dry spots developed on the grass surface | | |
|---|---|---|---|
| | A | B | C |
| Initial water content of the soil (depth 3 cm) | 9.5% | 4.0% | 4.0% |
| No. 1 | Not developed after 40 days | Not developed after 40 days | Not developed after 40 days |
| No. 2 | 40 days | 40 days | 32 days |
| No. 3 | Not developed after 40 days | 12 days | 23 days |
| No. 4 | 33 days | 15 days | 29 days |
| No. 5 | 30 days | 12 days | 27 days |
| No. 6 | 20 days | 7 days | 8 days |

(Test area C received 50 mm per unit area of water sprinkling, as rain simulation, after a week from spraying of the treatment agent.)

As shown above, the method of the present invention which jointly sprinkles aqueous solutions of the acetylene glycol derivative and the cationic water retentive agent (No. 1) can prevent development of dry spots for a long duration of time regardless of the water content of the soil or weather (rain) conditions. It is also shown that the method of the present invention which uses the water soluble polymer water retentive agent which is not a cationic water retentive agent also prevents development of dry spots for a long duration of time, but rain causes draining of the treatment agent and reduces the preventive effect (No. 2). It is also shown that the method of the present invention which sprinkles only the aqueous solution of the cationic water retentive agent does not have much effect on soil which has a low water content and already has dry spots, but can prevent development of dry spots for a long duration of time when sprinkled on soil with a high water content (No. 3).

What is claimed is:

1. A method for improvement and prevention of dry spots on the grass surface of a golf course consisting essentially of sprinkling of an acetylene alcohol derivative having the following formula:

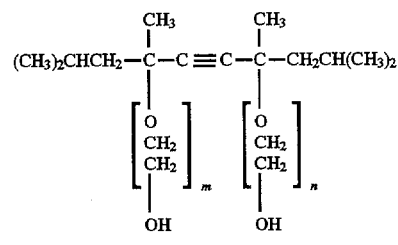

(m + n = 3.5)

on the grass surface.

2. A method for improvement and prevention of dry spots on the grass surface of a golf course as described in claim 1 wherein said acetylene alcohol derivative is a compound prepared by adding ethylene oxide to acetylene glycol.

3. A method for improvement and prevention of dry spots on the grass surface of a golf course as described in claim 1 wherein, when sprinkling said acetylene alcohol derivative, a water soluble polymer water retentive agent is jointly sprinkled.

4. A method for improvement and prevention of dry spots on the grass surface of a golf course as described in claim 3 wherein said water soluble polymer water retentive agent is a water retentive agent made of a cationic water soluble polymer.

5. A method for improvement and prevention of dry spots on the grass surface of a golf course as described in claim 2 wherein, when sprinkling said acetylene alcohol derivative, a water soluble polymer water retentive agent is jointly sprinkled.

6. A method for improvement and prevention of dry spots on the grass surface of a golf course as described in claim 5 wherein said water soluble polymer water retentive agent is a water retentive agent made of a cationic water soluble polymer.

* * * * *